United States Patent [19]

Banning et al.

[11] Patent Number: 4,834,709
[45] Date of Patent: May 30, 1989

[54] PREFORMABLE CATHETER

[75] Inventors: Robert D. Banning, St. Peters; Ronald Crouther, Chesterfield, both of Mo.; Thomas W. Davison, North Attleboro, Mass.

[73] Assignee: Sherwood Medical Company, St Louis, Mo.

[21] Appl. No.: 145,706

[22] Filed: Jan. 19, 1988

Related U.S. Application Data

[63] Continuation of Ser. No. 844,397, Mar. 26, 1986, abandoned.

[51] Int. Cl.⁴ .............................................. A61M 5/18
[52] U.S. Cl. .................................. 604/170; 604/282; 604/281
[58] Field of Search ...................... 128/341; 604/95, 8, 604/170, 280–283

[56] References Cited

U.S. PATENT DOCUMENTS

| 229,633 | 7/1880 | Pfarre | 128/341 |
|---|---|---|---|
| 1,060,665 | 5/1913 | Bell | 604/281 |
| 2,221,138 | 11/1940 | Hendrickson | 128/348 |
| 2,393,003 | 1/1946 | Smith | 128/349 |
| 2,458,305 | 1/1949 | Sanders | 128/348 |
| 3,128,769 | 4/1964 | Scislowicz | 128/348 |
| 3,152,592 | 10/1964 | Foley | 128/349 |
| 3,169,528 | 2/1965 | Knox, III et al. | 604/281 |
| 3,419,010 | 12/1968 | Williamson | 128/350 |
| 3,485,234 | 12/1969 | Stevens | 604/282 |
| 3,612,038 | 10/1971 | Halligan | 128/2.05 R |
| 3,612,058 | 10/1971 | Ackerman | 128/348 |
| 3,757,768 | 9/1973 | Kline | 604/170 |
| 3,825,001 | 12/1972 | Bennet et al. | 128/214.4 |
| 3,841,308 | 10/1974 | Tate | 128/2 M |
| 3,854,473 | 12/1974 | Matsuo | 128/8 |
| 3,867,945 | 2/1975 | Long | 604/170 |
| 3,923,066 | 12/1975 | Francisoud et al. | 604/170 |
| 3,973,556 | 6/1975 | Fleischhacker et al. | 128/2 M |
| 4,137,916 | 2/1979 | Killman et al. | 604/170 |
| 4,345,602 | 8/1982 | Yoshimura | 128/349 R |
| 4,362,163 | 12/1982 | Krick | 604/280 |
| 4,456,017 | 6/1984 | Miles | 604/95 |
| 4,504,268 | 3/1985 | Herlitze | 604/170 |
| 4,531,933 | 7/1985 | Norton et al. | 604/8 |
| 4,596,564 | 6/1986 | Spetzler et al. | 604/281 |
| 4,671,795 | 6/1987 | Mulchin | 604/8 |
| 4,713,049 | 12/1987 | Carter | 604/95 |

OTHER PUBLICATIONS

DLP Inc., Grand Rapids, Mich., "Left Hear Vent Catheters", Advertisement.

Primary Examiner—Stephen C. Pellegrino
Assistant Examiner—Kathleen A. Daley
Attorney, Agent, or Firm—Stanley N. Garber; Andrew J. Beck; William R. O'Meara

[57] ABSTRACT

A catheter and stylet assembly is provided which includes a silicone rubber catheter for insertion into the left ventricle of the heart. A stylet of malleable metal covered by a plastic cover is inserted into the catheter to permit the catheter and stylet to be manually shaped into a desired form before insertion into the patient. The stylet is removable from the catheter after the catheter is in the patient.

19 Claims, 1 Drawing Sheet

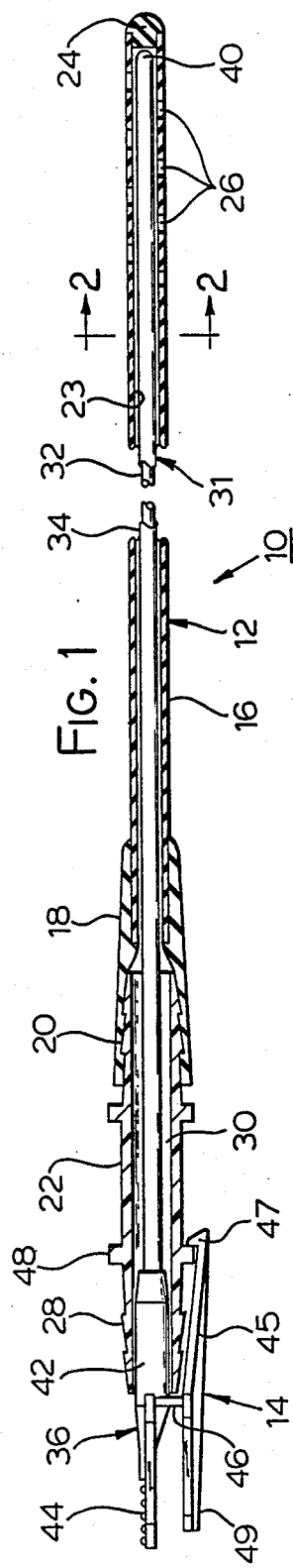
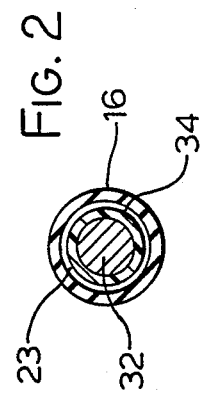
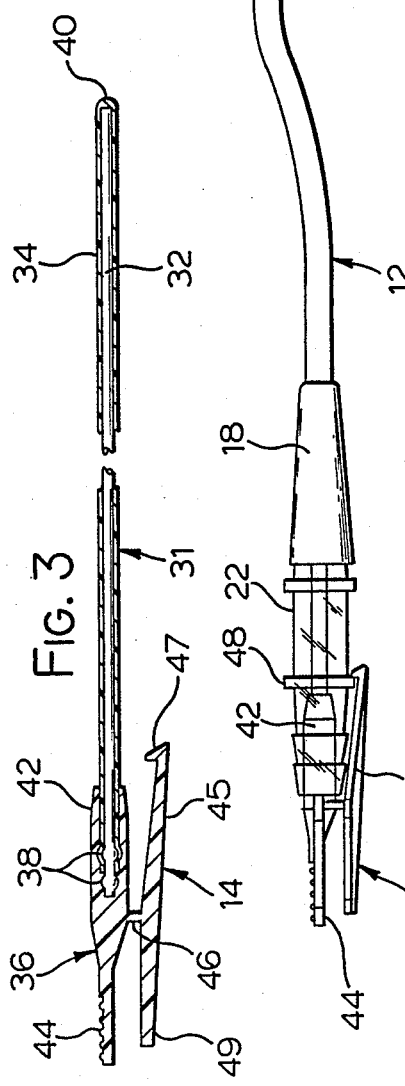
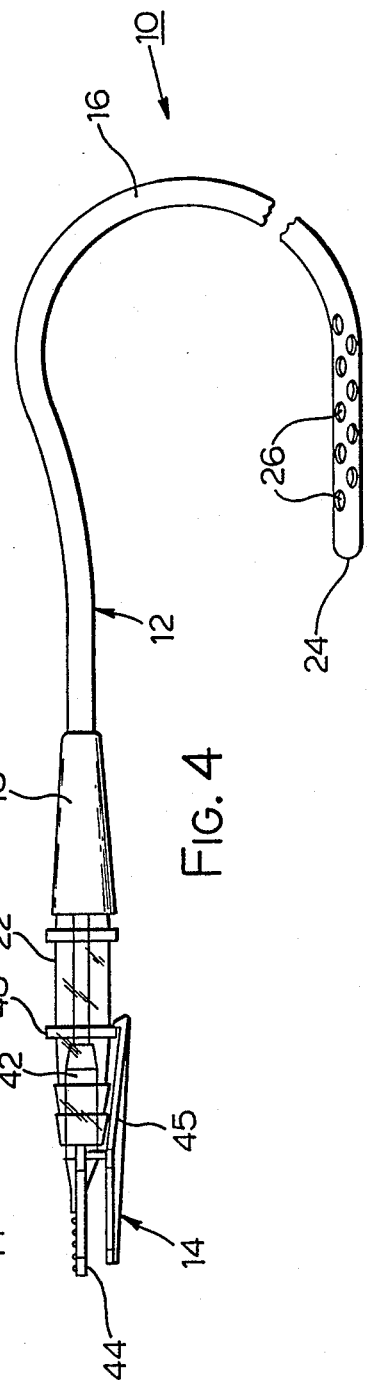

PREFORMABLE CATHETER

This is a continuation of co-pending application Ser. No. 844,397 filed on Mar. 26, 1986 now abandoned.

TECHNICAL FIELD

This invention relates to preformable catheters and more particularly to preformable elastomeric catheters and to malleable stylets for such catheters.

BACKGROUND ART

Cardiopulmonary bypass vascular catheters, for example, left atrial or left heart vent and left ventricular vent catheters, are used to drain fluid from the left ventricle to prevent excessive pressure build-up in the left heart portion during bypass surgery. The left atrial vent catheter may be inserted through the right superior pulmonary vein, left atrium, and mitral valve, and into the left ventricle. The left ventricular vent catheter may be introduced directly into the left ventricle through the ventricle wall. After insertion, the stylet is removed from the catheter and the catheter is connected to the extracorporeal system that includes artificial heart and lung apparatus.

Many such catheters have been made of polyvinyl chloride (PVC) and with a rigid plastic stylet or a malleable wire imbedded in a sidewall of the catheter. However, since heart surgery is now being performed at relatively low temperatures, conventional PVC catheters have become less desirable because they become relatively rigid and less flexible at the lower temperatures making the catheter more difficult to manipulate during insertion and removal from the patient. Also, with relatively stiff catheters there is greater risk of damage to the heart during the operation. For this reason, such catheters have more recently been made of silicone rubber which is soft and supple, and these characteristics are substantially not affected by the low temperatures encountered during surgery. Because silicone rubber catheters are soft and supple, there is less chance of damage to the patient during insertion and removal of the catheter as well as during the operation.

If the diameter of the stylet is excessively small, it may kink and bend excessively relative to the catheter making the manual preshaping of the catheter less accurate or controllable. Stylets have been formed of closely coiled stainless steel wire so that the stylet has a substantially larger diameter than that of the straight wire in order to more nearly fill the catheter lumen. In this way, the stylet can have a sufficiently large diameter relative to the catheter lumen so as to produce a catheter having sufficiently good handling and shaping characteristics, and yet have a high malleability due to the small size of wire used in the coiled stylet. However, coiled stainless steel wire stylets are relatively heavy and expensive compared to straight wire stylets. Catheters having a malleable wire embedded in the sidewall of the catheter have been used to allow shaping of the catheter prior to insertion but the suppleness or flexibility of such catheters while in the heart and vessels of the patient are limited by the presence of the wire which cannot be removed from the catheter. Non-malleable plastic such as nylon or high density polyethylene rods have been proposed as stiffeners but are generally limited to catheters that do not require manual preshaping.

SUMMARY OF THE INVENTION

It is therefore an object of the present invention to provide an improved catheter having a malleable stylet wherein one or more of the above undesirable features or problems are reduced or overcome. Another object of the present invention is to provide an improved malleable silicone catheter adapted for use as a cardiopulmonary bypass vascular catheter and which is provided with a stylet which is relatively highly malleable and yet of relatively large diameter and which is readily manually preformable and removable from the catheter. Still another object is to provide an improved malleable stylet which is economical in construction and which is easily manually shaped, will remain in its shaped condition until manually reshaped, and which is easily slidable from an elastomeric catheter.

In accordance with one aspect of the present invention, a flexible catheter is provided with a stylet that includes a malleable metal wire having a covering. In accordance with another aspect of the present invention, a stylet is provided which includes a malleable wire covered by a plastic covering adapted for use in an elastomeric catheter and which is slidably removable from the catheter. In accordance with still another aspect, a cardiopulmonary bypass catheter is provided which includes a silicone rubber catheter and a malleable stylet slidable relative to the catheter and including a malleable metal wire having a plastic covering.

These, as well as other objects and advantages of the present invention will become more apparent from the following detailed description and accompanying drawing.

FIG. 1 is a longitudinal cross-section view of a cardiopulmonary left atrial vent catheter in accordance with the present invention;

FIG. 2 is an enlarged cross-sectional view taken along line 2—2 of FIG. 1;

FIG. 3 is a longitudinal cross-sectional view of the stylet of FIG. 1; and FIG. 4 is a side view on a slightly reduced scale of the catheter of FIG. 1 but after it has been manually formed into a curved configuration.

DETAILED DESCRIPTION OF THE PREFERRED EMBODIMENT

Referring now to the drawings, and particularly to FIGS. 1 and 2, there is shown a cardiopulmonary bypass vascular catheter in the form of a left atrial vent catheter and stylet assembly 10. Assembly 10 includes a flexible catheter 12 and a stylet assembly 14.

Catheter 12 includes a flexible tube 16 which is preferably formed of an elastomer, preferably silicone rubber so that the tube is soft and supple. Tube 16 is provided with a conical or radially outwardly flaring funnel connector 18 at the proximal end of the tube which receives one end 20 of a double-ended tube connector 22. Tube 16 has a lumen 23 closed at the distal end by a catheter tip 24 having a smoothly rounded outer surface. Adjacent the distal end of tube 16 are a plurality of eyes or openings 26 extending through the sidewall of the tube 16. The funnel connector 18 may be formed of a suitable plastic and is preferably formed of silicone rubber. The funnel connector may be connected to the tube 16 by a suitable adhesive or bonding agent. The end 20 of tube connector 22 is connected to the funnel connector 18 by a tight frictional engagement fit. The end 20 has tapered portions tapering inwardly in the distal direction. The tip 24 is also preferably of silicone rubber and is fixed to the distal end of tube 16 such as by a suitable bonding agent, for example, and adhesive such as a silicone adhesive. The tube connector 22 has a proximal end 28 which has portions tapering inwardly in the proximal direction and is adapted for frictional connection with tubing (not shown), such as tubing of an extracorporeal artificial heart-lung system. The connector 22 has a bore 30 extending through it which is in fluid communication with catheter lumen 23.

As seen also in FIG. 3, the stylet assembly 14 is shown including a stylet 31 having an inner stylet rod or wire 32 extending within an outer covering 34 which may be a separately formed sleeve. The proximal ends of the stylet wire 32 and the covering 34 are fixed to and within a stylet handle 36 which may be formed or molded of a suitable plastic such as polyethylene or the like. The stylet wire 32 and covering 34 may be insert molded in handle 36 during the molding of the handle. The stylet is shown as having a pair of crimps 38 with the proximal end of tube 16 extending over the distal crimp. The proximal end of covering 34 is thus closed to the atmosphere. A spherical distal end tip 40 is provided at the distal end of covering 34. The rounded tip 40 may be formed by melt forming the distal end of sleeve 34. Tip 40 insures that the distal end of wire 32 does not pierce the catheter 12 when fully inserted into the catheter and it closes the distal end of sleeve 34 to the atmosphere. Thus, the entire wire 32 in the construction shown is completely enclosed by the covering 34 and handle 36, the covering completely enclosing the free surface of the wire while the handle covers the proximal end portion.

Handle 36 has a distal portion 42 which slidingly fits into the proximal end 28 of tube connector 22, and a proximally extending integral fixed arm 44. The handle has a pivotal latching arm 45 resiliently integrally connected intermediate its ends to the arm 44 by an integral resilient connection 46. The arm 45 has a latch 47 at the distal end that cooperates with an integral annular flange 48 on the tube connector 22. Arm 45 has an end portion 49 extending proximally from the resilient connection 46. The stylet handle 36 is shown in FIGS. 1 and 4 in the latched condition with the latch 47 engaging the distal side of flange 48 to prevent distal movement of the stylet 14 relative to the catheter 12. When in the latched condition, the stylet 14 extends to or substantially to the distal end of catheter lumen 23 or tip 24 as shown in FIG. 1. In this way, the stylet 14 is maintained in its desired fully inserted condition in catheter 12 so that the catheter and stylet can be inserted into a patient without the stylet moving longitudinally relative to the catheter and the distal end of catheter 12 bending excessively. When it is desired to remove the stylet from the catheter 12, the proximal end 49 of the latch arm 45 may be moved toward the arm 44, such as by pinching and 49 and arm 44, to unlatch the latch 47 from flange 48. This allows the stylet 14 to be withdrawn proximally from the catheter 12.

Stylet wire 32 is formed of a suitable malleable metal, such as aluminum or stainless steel, preferably, it is formed of solid aluminum. The covering 34 is preferably a plastic material and polypropylene is especially preferable because of its desirable characteristic of being readily slidable without undue force from its fully inserted condition as shown in FIGS. 1 and 4 to a fully removed condition (FIG. 3). Covering 34 may be made of other materials such as high density polyethylene, teflon (FEP or TFE) or polyacetal in some catheters. The stylet covering 34 may be a sleeve of plastic material such as an extruded sleeve or tube of polypropylene, although the covering 34 could be a coating applied while in liquid form and hardened or applied in any other suitable manner. Where an extruded sleeve is used, the diameter of the sleeve should be slightly larger than the wire to permit insertion of the wire into the sleeve during manufacture.

In use, with the stylet assembly 14 in place in catheter 12 as shown in FIG. 1, the surgeon may manually curve or bend the catheter 12 and stylet 31 into a desired configuration or shape for inserting the catheter and stylet assembly 10, tip first, into the patient and so that the distal end of the catheter is placed in the desired location within the patient, such as in the left ventricle. Once catheter 12 is in its desired location, the stylet assembly 14 is unlatched from connector 22, and withdrawn from catheter 12 and the tube connector 22 while maintaining the catheter tip 24 and openings 26 in the desired location in the patient.

Catheter 12, being pliable and formed of a soft material, such as silicone rubber, is substantially inert to the body and there is less chance of damage to the patient than when catheters of more rigid materials are employed. The malleable stylet 31 can be readily bent by the surgeon into the desired shape with the pliable catheter tube 16 taking on any shape that is assumed by the stylet. The stylet 31 is ductile or malleable and is readily manually shaped or deformed, and it maintains its new shape or deformed condition when released or freed of shaping forces. Since the stylet 31 is capable of being easily deformed and maintains its deformity permanently or until reshaped, the supple catheter 12 surrounding the stylet is, of course, similarly deformed or shaped and remains deformed by the stylet. At the same time, the stylet 31 causes the assembly 10 to be sufficiently stiff so as to be inserted or worked into its desired final location within the patient without an undesirable amount of effort. As previously mentioned, the rounded tip 40 of stylet 14 aids in ensuring that the soft silicone rubber catheter tube 16 is not inadvertently pierced by the stylet wire 32 during typical insertion procedures. Since the metal 2 is completely enclosed by the covering 34 and the handle 36, blood cannot contact the metal wire, although such contact does not necessarily produce undesirable effects.

It has been found that when the covering 34 is of polypropylene, the stylet readily slides on the silicone rubber sidewalls of lumen 23 substantially without sticking and even though the stylet and catheter may be curved or bent. This allows the stylet assembly 14 to be easily removed from catheter 14 while maintaining the catheter 12 in place within the patient. By employing a covering such as covering 34, the diameter of the stylet is effectively increased without increasing the size of wire 32 and thereby decreasing the malleability of the stylet. The stylet 31 is desirably of a relatively large diameter, that is, a diameter that approaches but is less than that of catheter lumen 23. The stylet should, of course, not be so large as to require undue effort in removing the stylet from the catheter. By employing a stylet of relatively large diameter, such as stylet 31, good bending and insertion control characteristics with less flexing of the catheter relative to the stylet are obtained. Thus, the necessity of coiling a wire of small diameter in order to obtain a stylet having an effectively larger diameter for good insertion characteristrics is not necesary in the catheter and stylet assembly 10.

In one example, a catheter and stylet assembly included a silicone rubber catheter having a lumen with a diameter of about 0.12 inch (3.048 mm), and a stylet having an outer diameter of about 0.1 inch (2.54 mm). The style had a solid aluminum wire having an outer diameter of about 0.062 inch (1.57 mm) and a covering sleeve cut from extruded polypropylene tubing having an inner diameter of about 0.067 inch (1.702 mm) and an outer diameter of about 0.1 inch (2.54 mm), these being nominal or average values. The outer diameter of the wire was slightly less than the inner diameter of the covering to allow insertion of the wire into the covering during manufacture of the stylet. Thus, while the outer diameter of such wire was only about one-half of that of the catheter lumen, the overall outer diameter of the stylet, including the polypropylene covering, was about 5/6 or 83% of the diameter of the catheter lumen and provided good handling characteristics. About one-third of the total thickness of the stylet, as measured along the diameter of a cross-section of the stylet, is provided by the cover, and the cross-sectional area of the cover was greater than that of the wire. The above stylet may be used with a larger catheter such as one having a lumen with a diameter of about 0.162 inch (4.115 mm). In the latter case, the diameter of the stylet is still more than one-half (about 3/5) of that of the diameter of the larger catheter lumen.

In the case of a left ventricular vent catheter, the catheter and stylet assembly can be made identical to assembly 10 except that the catheter holes will not generally be placed as far from the distal end of the catheter as they are in a left atrial vent catheter. Also, depending upon the use to which the catheter is to be put, the catheter tube material may be of a suitable thermoplastic polyurethane, latex rubber or the like instead of the preferred silicone rubber.

It should be understood that although the invention has been described with reference to the illustrated embodiment, modifications thereto may be made without departing from the true spirit and scope of the invention.

What is claimed is:

1. A catheter and stylet assembly comprising a tube of flexible material adapted for insertion into a patient and having a lumen extending therein, and a stylet assembly removalby insertable into said lumen including only one malleable metal wire, tubular cover means surrounding and covering at least a major portion of said wire including a portion adjacent the distal end of said wire, and a handle connected to proximal end portions of said wire and said tubular cover means, said tubular cover means having an inner diameter sufficiently greater than the outer diameter of said wire so as to allow insertion of said wire into said tubular cover means during assembly of said stylet.

2. The assembly of claim 1 wherein said tube is of an elastomeric material, and said cover means is of a plastic material which is slidable relative to said tube while in contact with said tube.

3. The assembly of claim 1 wherein said material is silicone rubber.

4. The assembly of claim 3 wherein said cover means if of polypropylene.

5. The assembly of claim 1 wherein said wire is of malleable aluminum.

6. The assembly of claim 1 wherein said cover means includes a sleeve extending distally beyond the distal end of said wire and closed at its distal end to cover the distal end of said wire.

7. The assembly of claim 1 wherein the proximal ends of said wire and said cover means are sealingly fixed within said handle with said handle and cover together completely enclosing said wire.

8. The assembly of claim 7 wherein said lumen is closed at the distal end of said tube, and said tube has a plurality of openings extending through the sidewalls of said tube adjacent to but spaced from the distal end of said tube, said tube is formed of silicone rubber, and said cover means includes a plastic layer slidable relative to said tube while in contact therewith.

9. The assembly of claim 7 wherein a proximal end portion of said cover means extends into said handle and said cover means is tubing receiving said wire and completely covering the entire free surface of said wire from the distal end thereof to to said handle.

10. The assembly of claim 9 wherein said wire is of aluminum and solid in cross-section and substantially straight.

11. The assembly of claim 1 wherein the cross-sectional area of said cover means is greater than that of said wire.

12. The assembly of claim 1 wherein the outer diameter of said stylet is at least 60% of the diameter of said catheter lumen.

13. The assembly of claim 12 wherein the outer diameter of said stylet is about 80% of the diameter of said catheter lumen.

14. The assembly of claim 1 wherein said cover means is a portion of a tubular plastic extrudate and wherein said wire and said cover means are generally straight and bendable.

15. The assembly of claim 1 wherein said handle includes releasable latching means for releasably securing said handle to the proximal end portion of said tube with said stylet extending in said tube.

16. A cardiopulmonary bypass vascular catheter comprising a catheter of silicone rubber having a lumen closed at the distal end, said catheter having a plurality of openings adjacent the distal end extending through the sidewall thereof, and a stylet removably insertable into said lumen and extending substantially to the distal end of said lumen when fully inserted therein, said stylet including only one malleable metal wire, a tubular sleeve of a plastic material covering substantially the entire outer surface of said wire, and a handle connected to the proximal end portions of said sleeve and said wire, said tubular sleeve means having an inner diameter sufficiently greater than the outer diameter of said wire so as to allow insertion of said wire into said tubular sleeve means during assembly of said stylet.

17. The catheter of claim 16 wherein said sleeve is of a plastic which is slidable without sticking while in contact with said catheter.

18. The catheter of claim 17 wherein said plastic of said sleeve is a polypropylene.

19. The catheter of claim 1 wherein said cover means is a tubular extrudate and said wire is insertable into said extrudate.

* * * * *